United States Patent [19]

Balint et al.

[11] Patent Number: 4,764,607
[45] Date of Patent: Aug. 16, 1988

[54] METHOD FOR RECOVERING CAPROLACTAM

[75] Inventors: Laszlo J. Balint, Chester; Julius Greenburg, Richmond, both of Va.

[73] Assignee: Allied Corporation, Morris Township, Morris County, N.J.

[21] Appl. No.: 945,117

[22] Filed: Dec. 22, 1986

[51] Int. Cl.$^4$ .......................................... C07D 201/16
[52] U.S. Cl. .................................... 540/540; 203/58; 203/57
[58] Field of Search ........................................ 540/540

[56] References Cited

U.S. PATENT DOCUMENTS 2,758,491 8/1956 Kretzers et al. .................... 540/540
3,485,820 12/1969 Hofmann et al. ................... 540/540

FOREIGN PATENT DOCUMENTS 7209438 1/1973 Netherlands ....................... 540/540

Primary Examiner—Robert T. Bond
Attorney, Agent, or Firm—Richard A. Anderson

[57] ABSTRACT

Method and improved apparatus for recovering a volatile organic material, such as caprolactam, from a liquid mixture of organic and inorganic materials are disclosed. The method features the step of mixing the liquid mixture with superheated steam for 0.005 to 1.0 second to vaporize a large portion of the volatile organic material without degrading the organic materials. The steam and vaporized organic materials are then separated from the liquid mixture remaining, followed by separation of the vaporized organic material from the steam. The vaporized organic material subsequently is condensed. The improved apparatus features means for introducing superheated steam into a vaporizer feed pipe, as well as means for mixing the superheated steam with the liquid mixture in the pipe for 0.005 to 1.0 second so that a large portion of the volatile organic material is vaporized and feeds with the steam and remaining liquid mixture into the vaporizer for separation.

18 Claims, 3 Drawing Sheets

METHOD FOR RECOVERING CAPROLACTAM

BACKGROUND OF THE INVENTION

This invention relates to a method and improved apparatus for recovering a volatile organic material from a liquid mixture of organic and inorganic materials. More particularly, the present invention is a method and improved apparatus for recovering epsilon-caprolactam or other heat-sensitive materials from organic and inorganic process residues by mixing the material to be processed with superheated steam in a pipeline prior to entry into a vaporizer.

THE PRIOR ART

Epsilon-caprolactam, hereinafter generally called "caprolactam" or "lactam," is a valuable starting material for production of synthetic linear polyamides having utility in the form of filaments, extruded articles molded articles, etc. A very high purity caprolactam is required to assure good quality in polyamides produced therefrom.

Crude caprolactam is purified by crystallization or by distillation. Crystals of purified caprolactam are recovered, and an aqueous mother liquor containing various impurities is separated. To this mother liquor other caprolactam-containing streams are added from other parts of the production process, e.g., regenerated caprolactam from the depolymerization of polyamide waste, wash waters from polymer chip washing, and waste waters from spills. These streams are combined in diluted form. Standard distillation of the combined streams leaves a liquid mixture of organic and inorganic materials containing about 40 to 60 percent caprolactam and about 40 to 60 percent heavy residues.

Since it is not economical to discard this caprolactam, methods have been developed to recover as much as possible. A steam distillation recovery method is taught by U.S. Pat. No. 4,582,642 to Crescentini et al., hereby incorporated by reference. A liquid mixture containing about 50 percent caprolactam is charged to a vessel, and superheated steam is sparged (350° C.) from beneath a pool of the liquid mixture. Caprolactam-steam vapors produced are passed to a partial condenser from which a cprolactam-rich condensate is removed. This method has several undesirable results. The processed fluid is heated for a long period of time, on the order of eight to nine hours, which results in cross-linking; this degrades the desirable organic by producing volatile color bodies which are entrained by the organic. Sparging also causes bumping of the vessel (vaporizer) which can result in carryover of the tar-like residues into the desired product. Also sparging causes excessive condensation of moisture in the tar-like residue leaving the vessel (bottoms); this causes foaming of the residue which makes it difficult to handle and decreases its ability to solidify.

The present invention was developed to overcome these disadvantages of the prior art. It also has utility in the recovery of volatile organic materials.

SUMMARY OF THE INVENTION

In the present invention, the method of recovering a volatile organic material from a liquid mixture of organic and inorganic materials comprises the steps of:
  a. mixing the liquid mixture with superheated steam for 0.005 to 1.0, more preferably 0.01 to 0.10, second to vaporize a large portion of the volatile organic material without degrading the organic and inorganic materials;
  b. separating the vaporized organic material and the steam from the liquid mixture remaining;
  c. separating the vaporized organic material from this steam; and
  d. condensing the vaporized organic material.

The superheated steam is at a temperature of 400° to 600° C., more preferably 450° to 550° C., and is fed at a rate of 0.5 to 2.0 times that of the liquid mixture, or as needed by the energy balance of the system. For a given volatile material, an energy balance is established between temperature, feed ratio and rate. The key is vaporization of the volatile material without degradation. By "a large portion" of the volatile organic material is meant at least 80, preferably 90, percent. By "degrading" the organic materials is meant two things: that cross-linking occurs and/or that other, undesirable volatiles are stripped which will be seen as color or permanganate number.

The liquid mixture preferably comprises 25 to 70, more preferably 40 to 60 weight percent caprolactam, and the method is directed to the recovery of caprolactam.

The present invention also provides an improved method for recovering caprolactam from a liquid mixture of organic and inorganic materials wherein the liquid mixture is fed through a pipe to a vaporizer. The improvement comprises:
  a. mixing the liquid mixture with superheated steam in the pipe prior to entry into the vaporizer for 0.005 to 1.0 second to vaporize a large portion of the caprolactam;
  b. separating the vaporized caprolactam and the steam from the liquid mixture remaining in the vaporizer;
  c. separating the vaporized caprolactam from the steam; and
  d. condensing the vaporized caprolactam.

The apparatus of the present invention represents an improvement in a system that comprises a pipe for feeding the liquid mixture into a vaporizer which further comprises an exhaust for removal of the vaporized material and an outlet for the discharge of unvaporized residues. The improvement comprises means for introducing superheated steam into the pipe, and means for mixing the superheated steam with the liquid mixture in the pipe for 0.005 to 1.0 second, so that a large portion of the volatile organic material is vaporized and feeds with the steam and remaining liquid mixture into the vaporizer for separation. The system preferably further comprises a baffle which is located inside the vaporizer such that the vaporized material, the steam and the remaining liquid mixture discharge from the pipe to impinge upon the baffle.

The mixing means may be any mixing device which creates turbulent flow characteristics and a high flow rate in the pipe. The mixing must be such that the dynamic effect of the highly turbulent steam stream provides an almost instantaneous heat transfer into the liquid feed, thus providing the heat of vaporization to the lighter volatile compound. The mixing device may be a simple pipe or bundle of pipes where the flow has turbulent characteristics; a pipe or bundle of pipes provided with static mixer elements; a channel spiral accompanied by high flow rate; venturi mixers combined with pipes, etc.

In addition to being economical, this invention offers several other advantages over the prior art. The short contact time (milli-seconds) between the liquid mixture and the superheated steam reduces degradation and cross-linking, and results in less volatile color-body formation. No "bumping" occurs to vibrate the vessel; gross carryover of residue is thus eliminated. The residues exiting the bottom of the vessel contain minimum moisture, reducing foaming tendancies and thus, them easier to handle and solidify.

This invention may be used in any caprolactam producing plant to recover product from residues. However, it may also be used in other organic syntheses where heat-sensitive organics are to be recovered. For example, fatty acids, such as stearic acid, or a mixture of fatty acids (saturated and unsaturated) can be recovered from raw product obtained by hydrolysis of fats. Also, heavy volatile petroleum derivatives can be recovered from tail streams, tar-like residues of refining processes.

The invention will be more clearly understood and additional objects and advantages will become apparent upon reference to the discussion below and to the drawings and examples which are given for illustrative purposes.

The values for PN and color were obtained by Allied Standard Test Methods No. 189 (1/67) and No. 230 (4/67) published by Allied Corporation from Morristown, N.J. The PN method is also described in U.S. Pat. Nos. 3,406,167 to Cheng et al. and 3,021,326 to Snider et al., both of which are hereby incorporated by reference.

DETAILED DESCRIPTION OF THE INVENTION

Figure 1:
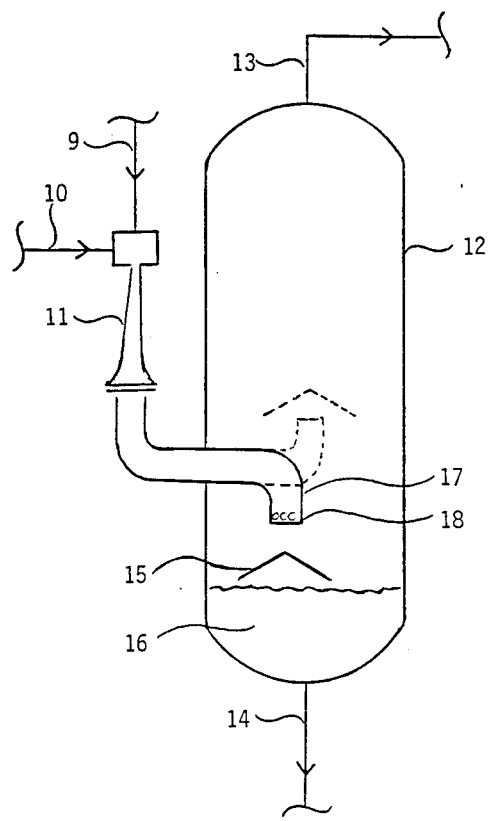
FIG. 1 is a vertical cross-section of the recovery system of the present invention with mixing eductor 11.
Figure 2:
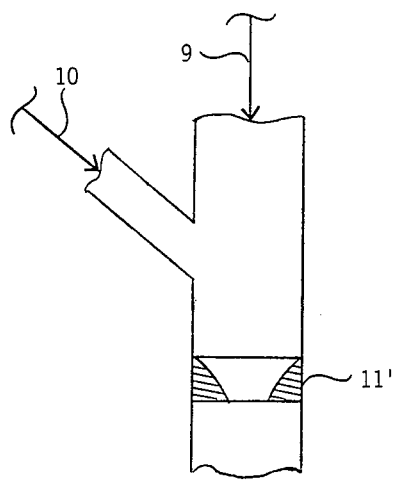
FIG. 2 is a cross-section of the introductory portion of FIG. 1 wherein venturi 11' is the mixing device.
Figure 3:
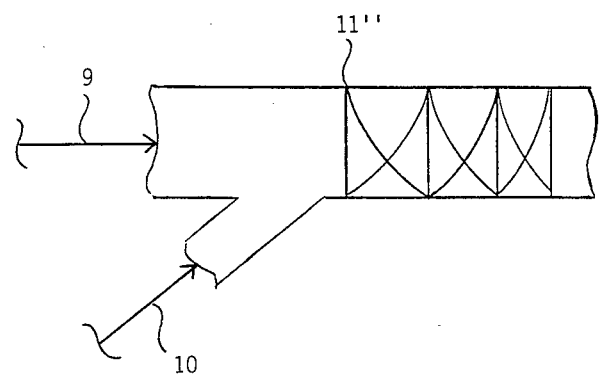
FIG. 3 is a similar view wherein static mixing elements 11" form the mixing device.

Reference is made to the drawing figures and accompanying description of U.S. Pat. No. 4,582,642 for an understanding of the prior art. In the prior art, the liquid feed mixture was charged to a vessel (vaporizer) via a pipe which discharged below the surface of a liquid pool of the material. Superheated steam was introduced by way of a different pipe and sparged below the surface of the liquid pool. The liquid mixture was exposed for eight to nine hours to superheated steam, bubbling through the liquid head/pool. The vaporized caprolactam-steam mixture produced during this bubbling was taken off overhead for separation in a conventional rectifying system. As will be shown in Example 1, the percentage of caprolactam removed by this system is much lower than with the system of the present invention.

With reference to the accompanying drawings, like numbers indicate like apparatus. Feed containing about 20 to 75 percent, more preferably 40 to 60 percent, caprolactam is fed at 9 to mixing eductor 11, to which superheated steam is fed from 10. The resulting mixture flashes into vaporizer 12 via pipe 17 with either a plurality of apertures 18 at its exit end or else the entire end opened, preferably the latter. Baffle 15 is located beneath exit end of pipe 17 and is the barrier against which pipe 17's contents are hurled. About 85 to 95 percent of the caprolactam from the original feed vaporizes in pipe 17 and exits through overhead line 13 of vaporizer 12 with the steam. The residue, which contains about 5 to 15 percent caprolactam, pools 16 at the base of vaporizer 12 for its ultimate exit via line 14 for disposal. Downstream of line 13, the vaporized caprolactam and steam mixture then undergo separation in a conventional rectifying system, e.g. a packed tower or partial condenser or similar concentrating system, unshown. Alternatively, the vaporized caprolactam and steam mixture could be condensed and the condensate recycled into the main process stream. With further reference to FIG. 1, pipe 17 may have an upward deflection with baffle 15 placed above its exit end, as shown in phantom.

Figure 4:
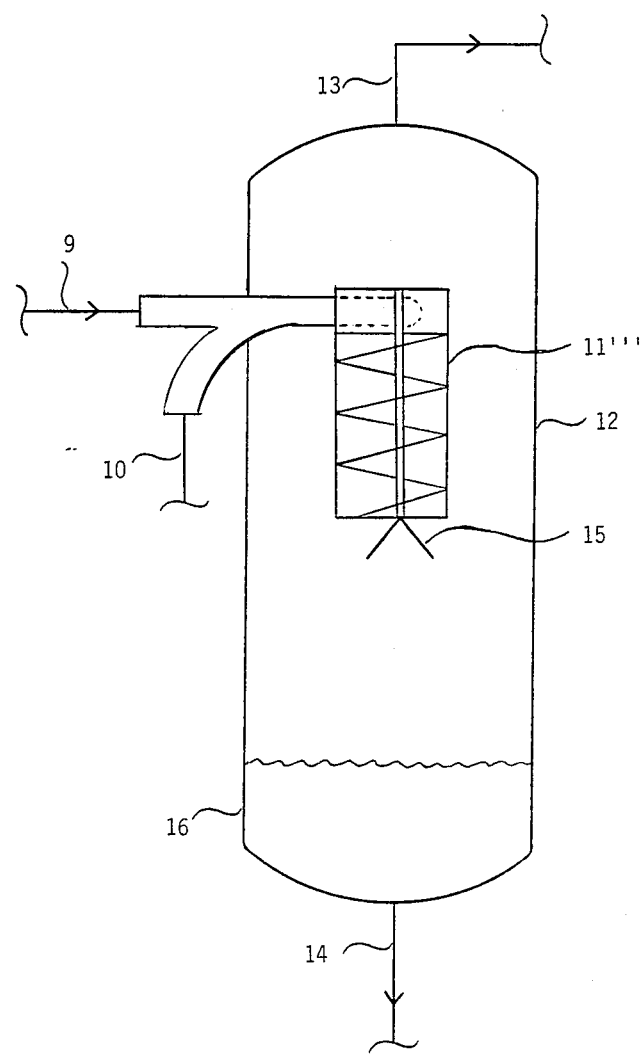
FIG. 4 is a view similar to FIG. 1 and wherein the system utilizes channel spiral 11''' as the mixing device.

An alternate embodiment of the present invention is shown in FIG. 4 where channel spiral 11''' is used as the mixing device in lieu of mixing eductor 11. The depicted spiral, which has 6 flights, provides an excellent turbulent flow path for the mixed steam and liquid feed.

The key advantage to the present invention is the almost instantaneous transfer of heat into the liquid feed, thus providing the heat of vaporization to the lighter, volatile compound, caprolactam. When the superheated motive steam is mixed with the materials to be treated in a pipe, a very thin film is produced on the wall of the pipe where the steam and liquid run together. The highly turbulent steam provides continuous eddies and thus an extensive exposure of the molecules to a continuously renewed surface, from which the volatile (caprolactam) moves into the gas phase by diffusion. Surprisingly, less than one second contact time is required to efficiently remove (by vaporization) caprolactam from the feed mixture as compared to the approximately eight to nine hours (with lower efficiency) of the prior art.

In Examples 1-3, the average of data collected in a commercial plant over a period of several months is presented.

EXAMPLES 1 AND 2 (COMPARATIVE)

Feed containing about 60 percent caprolactam was charged to a vaporizer at a rate of 5000 lb/h (0.63 kg/s) and at a temperature (preheated) of 140° C. This feed was introduced beneath the surface of pooled residue. Superheated steam at a temperature of 540° C. was fed at a rate of 5000 lb/h (0.63 kg/s) to the same vaporizer. The steam was distributed by a sparge ring located beneath the surface of pooled residue. The residue, which was removed at a rate of 2000 lb/h (0.25 kg/s), was at a temperature of about 200° to 210° C. in Example 1 and about 220° to 235° C. in Example 2. Pooled residue volume and residence time were, respectively, about 51,600 lb (23,375 kg) and 8.9 h. The pressure of the system is given by the pressure drop caused by the back pressure of pipes and other equipment. Normally, it is 2 to 5 psig. The caprolactam-steam mixture produced during sparging was fed into a ten plate tower for separation. Water with traces of caprolactam was removed as overhead.

In Example 1, the amount of caprolactam in the residue removed from the vaporizer was about 29 to 30 weight percent. Color recovered in the caprolactam was 1500 to 2200 units.

In Example 2, the amount of caprolactam in the residue removed from the vaporizer was about 8 to 23 weight percent. The color recovered in the caprolactam was about 5000 to 6500 units.

With this process, the amount of crude caprolactam required to make 1000 pounds of virgin caprolactam was 1017 pounds.

EXAMPLE 3

Feed containing about 60 percent caprolactam was fed to mixing eductor 11 at a rate of 5800 lb/h (0.73 kg/s) and at a temperature (preheated) of 140° C. Superheated steam at 540° C. was fed to mixing eductor 11 at a rate of 5500 lb/h (0.70 kg/s). The steam/feed mixture was at a temperature of 226° C. The mixture flashed into vaporizer 12 where about 90 percent of the caprolactam from the feed mixture was removed through overhead line 13 with the steam. Less than 500 lb/h (0.06 kg/s) of superheated steam (540° C.) was distributed by a sparge ring located beneath the surface of pooled residue. The residue exited vaporizer 12 at a rate of about 2000 lb/h (0.25 kg/s) and at a temperature of about 226° C. The residence or holdup time and volume in vaporizer 12 were, respectively, 2.4 hours and 14,100 lb (6,387 kg). Contact time between the feed mixture and superheated steam was approximately 0.08 second. The caprolactam-steam mixture was removed from vaporizer 12 and separated as in Examples 1 and 2. The percent caprolactam in the residue removed from vaporizer 12 was about 10.5. Color recovered in the caprolactam was about 1900 to 2000 units. The number of pounds of crude caprolactam required to make 1000 pounds of virgin caprolactam was approximately 1009 pounds.

Clearly, when comparing Example 3 with either of Examples 1 or 2, one can see the tremendous advantage of the present system. Although the color recovered in the caprolactam was comparable in Examples 1 and 3, the percent caprolactam in residue was significantly higher in Example 1. With respect to Example 2, although the percent caprolactam in residue is comparable or better some of the time in Example 1, the color recovered in the caprolactam was approximately double that of Example 3. This is an indication of higher degree of impurities.

Certainly it can be seen that the present system is more economical. The system of Example 3 requires 8 pounds less of crude caprolactam to make 1000 pounds of virgin caprolactam. For every 100,000,000 pounds per year produced, this represents a savings of 800,000 pounds of caprolactam, quite a significant number.

EXAMPLES 4-7

The procedure of Example 3 was repeated with the changes shown in Table 1 (and no sparge ring). Table 1 also indicates percent caprolactam recovered as well as the color recovered in the caprolactam.

With reference to Table 1, it can be seen that the efficiency of caprolactam recovery increases with the steam feed to liquid mixture feed ratio. With reference to Example 5, a reduced rate of flow improved product quality (low color recovered) but the caprolactam content of the residue was high. Extreme stripping with a high steam feed to liquid mixture feed ratio (Example 7) reduced the caprolactam content in the residue; however the color recovered in the caprolactam was worse.

TABLE 1

| Example | Steam to Liquid Feed Ratio and Rates (lb) | Steam Temp. °C. | Caprolactam % Residue | Caprolactam % Recovered | Color* | PN |
|---|---|---|---|---|---|---|
| 4 | 1.2:1(42/34) | 509 | 13.4 | 82.7 | 1823 | 2600 |
| 5 | 1.3:1(29/22) | 553 | 14.3 | 86.8 | 878 | 1600 |
| 6 | 1.4:1(48/34) | 516 | 8.9 | 91.8 | 1965 | 3000 |
| 7 | 1.7:1(41/24) | 550 | 4.8 | ~100 | 2832 | 4350 |

*Color of ≦2000 is considered excellent quality.

EXAMPLES 8-10

The procedure of Example 3 is repeated in each of Examples 8, 9 and 10 with the substitution of venturi mixer 11', static mixing elements 11''', and channel spiral 11''', respectively. Excellent efficiencies and purity are obtained.

We claim:

1. A method of recovering a volatile organic material from a liquid mixture comprising the steps of:
   a. mixing the liquid mixture with superheated steam for 0.005 to 1.0 second to vaporize a large portion of the volatile organic material without degrading the organic materials;
   b. separating the vaporized organic material and the steam from the liquid mixture remaining;
   c. separating the vaporized organic material from the steam; and
   d. condensing the vaporized organic material.

2. The method of claim 1 wherein the volatile organic material is caprolactam.

3. The method of claim 1 wherein the liquid mixture and the superheated steam have a contact time of 0.01 to 0.10 second.

4. The method of claim 1 wherein the superheated steam is at a temperature of 400 to 600° C.

5. The method of claim 4 wherein the superheated steam is at a temperature of 450° to 550° C.

6. The method of claim 4 wherein the superheated steam is fed at a rate that is 0.5 to 2.0 times that of the liquid mixture.

7. In a method of recovering caprolactam from a liquid mixture wherein the liquid mixture is fed through a pipe to a vaporizer, the improvement comprising:
   a. mixing the liquid mixture with superheated steam in the pipe prior to entry into the vaporizer for 0.005 to 1.0 second to vaporize a large portion of the caprolactam;
   b. separating the vaporized caprolactam and the steam from the liquid mixture remaining in the vaporizer;
   c. separating the vaporized caprolactam from the steam; and
   d. condensing the vaporized caprolactam.

8. The method of claim 7 wherein the liquid mixture and the superheated steam have a contact time of 0.01 to 0.10 second.

9. The method of claim 7 additionally comprising the step of sparging superheated steam through the remaining liquid mixture in the vaporizer.

10. The method of claim 7 wherein the superheated steam is at a temperature of 400 to 600° C.

11. The method of claim 10 wherein the superheated steam is fed at a rate that is 0.5 to 2.0 times that of the liquid mixture.

12. The method of claim 11 wherein the liquid mixture comprises about 25 to 70 weight percent caprolactam; the liquid mixture and the superheated steam have a contact time of 0.01 to 0.10 second; and wherein the superheated steam is at a temperature of 450 to 650° C.

13. The method of claim 12 wherein the liquid mixture comprises about 40 to 60 weight percent caprolactam.

14. In a system for recovering a volatile organic material from a liquid mixture, said system comprising a pipe for feeding the liquid mixture into a vaporizer which further comprises an exhaust for removal of vaporized material and an outlet for the discharge of unvaporized material, the improvement comprising:
  a. means for introducing superheated steam into the pipe; and
  b. means for mixing the superheated steam with the liquid mixture in the pipe for 0.005 to 1.0 second; so that a large portion of the volatile organic material is vaporized and feeds with the steam and remaining liquid mixture into the vaporizer for separation.

15. The improved system of claim 14 further comprising a baffle, said baffle being located inside said vaporizer such that the vaporized material, the steam and the remaining liquid mixture discharge from the pipe to impinge upon the baffle.

16. The improved system of claim 14 wherein said means for mixing comprises a plurality of static mixing elements.

17. The improved system of claim 14 wherein said means for mixing comprises a mixing eductor.

18. The improved system of claim 14 wherein said means for mixing comprises a channel spiral.

* * * * *